United States Patent [19]

Nguyen

[11] Patent Number: 5,080,973
[45] Date of Patent: Jan. 14, 1992

[54] LOW FRICTION HIGH RELEASE COATINGS FOR RELEASE TAPES

[75] Inventor: Thanh V. Nguyen, Painesville, Ohio

[73] Assignee: Avery Dennison Corporation, Pasadena, Calif.

[21] Appl. No.: 527,028

[22] Filed: May 22, 1990

[51] Int. Cl.$^5$ .............................................. B32B 7/12
[52] U.S. Cl. ................................... 428/352; 428/343; 428/447; 428/351; 525/477; 525/478; 604/389; 604/390
[58] Field of Search .............. 428/447, 451, 343, 352; 604/389, 390; 525/477, 478

[56] References Cited

U.S. PATENT DOCUMENTS

| | | | |
|---|---|---|---|
| 4,521,471 | 6/1985 | Merrill | 428/40 |
| 4,591,622 | 5/1986 | Blizzard et al. | 525/478 |

Primary Examiner—Merrell C. Cashion, Jr.
Assistant Examiner—D. S. Nakarani
Attorney, Agent, or Firm—Christie, Parker & Hale

[57] ABSTRACT

A release surface for use in diaper tape assemblies comprises a cured release coating of a reactive silicone system comprising at least 15% by weight of a reactive polydialkyl siloxane, at least 40% by weight of a defined reactive silicone high adhesion agent and a silicone crosslinking agent. Cure occurs in the presence of Group VIII metal catalyst, and cured release coating has a coefficient of friction of less than about 0.7 lb/2 inch and a release greater than 50 g/in.

19 Claims, 1 Drawing Sheet

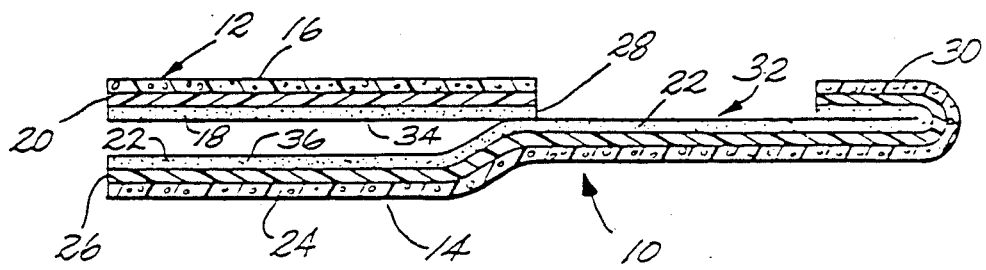

LOW FRICTION HIGH RELEASE COATINGS FOR RELEASE TAPES

FIELD OF THE INVENTION

The invention is directed to a low friction, high adhesion release coating for polypropylene film (tapes) used for disposable diaper tapes.

BACKGROUND OF THE INVENTION

Tape constructions for disposable diapers and their manufacture and assembly are described for instance in U.S. Pat. Nos. 4,171,239 to Hirsch et al. and 4,378,800 to Schaar each incorporated herein by reference.

Two different but cooperating tapes are used in disposable diaper tape manufacture. Each can consist of a polyolefin film having a release coating on one surface and a pressure sensitive adhesive on the opposed surface. One is known as a fastening tape and used in practice to close the diaper. The other is a release tape whose function is to protect the adhesive of the fastening tape until used.

They are combined at a "Y" junction with each tape supplying pressure-sensitive adhesive for bonding to the diaper shell. The release tape has its release layer against the adhesive of the fastening tape until use. They are manufactured from pressure-sensitive adhesive tapes on self-wound rolls—each having an adhesive on one side of a carrier film (e.g. polypropylene) and a cured release coating on the other.

The process of manufacture involves in-line folding of each tape, laminating them together, cutting to length and applying the combination to the diaper. Diapers are manufactured in a continuous web which passes through a tape lamination, cutting and application station.

More particularly, the fastening tape is folded over on itself at one end to form a fingerlift or tab, a thickened area to assist the user in grasping the "Y" end of the fastening tape and separate it from the release surface of the release tape. The release tape fold is used to create a strong bond at the edge of the diaper. The adhesive of the release tape and a portion of the adhesive of the fastening tape are bonded to opposed surfaces of a diaper construction. The balance of the fastening tape is secured to the release surface of the release tape.

Various joining and folding processes occur. The joining process involve changes in tape direction including a right angle turn which completes the fold.

If the tape encounters any significant drag on means to guide the tape through a turn, unequal tensions will form and cause the edge to wander. This gives poor alignment of the fold and inconsistent width to the folded edge.

After both folds are made the tapes are laminated together by aligning them prior to bringing them together. This alignment process involves passing the tapes over guide bars which contact the release surfaces of the tapes. Again, differential drag across the guide bars prevents smooth lamination since one tape may be traveling at a different speed relative to the other. Poorly aligned laminated tapes are difficult to guide through the remainder of the process and may have poor appearance.

The release surface of the release tape surface must also provide a fairly high bond to the fastening tape adhesive. This ensures the two tapes will stay together during the cutting and actual application to the diaper shell. It is particularly important while the lamination is being applied to the diaper shell. When the laminated tapes are cut and applied to the bottom of the formed diaper, the tapes are positioned so that the fastening tape/the release tape laminate extends beyond the edge of the formed diaper. A jig is used to guide the free end around the edge of the diaper. All of this occurs while the diaper moves at significant speed. A low bond strength between the fastening tape adhesive and the release tape at this application may allow the lamination to open during the severe turn and lead to a defective product.

In the past the cured release coating has been tin catalyzed. This has resulted in variable release and unwind performance in consequence of post curing (continuation of cure after the initial cure) of the applied release coating in the roll with release properties being somewhat dependent on how long bulk rolls were kept in inventory before moving the rolls into diaper production operations. It is understandably desirable to have available a low friction release coating to allow tape to slide over fixed posts used to change direction in tape alignment and joining operations in the manufacture of the diaper tape. By the same token, the adhesion or release level (force to cause release) must be sufficiently high to provide sufficient unwind tension to keep the release tape in a guide and prevent premature unraveling of the roll. Release is also important to keep the fastening tape/release tape combination together as it progresses through manufacturing operations. High release is also necessary to prevent the fastening tape from "flagging" as the lamination is folded around a diaper and to stay on the release surface of the release tape up to the time of use.

Prior silicone release coating do not provide stable low friction and high adhesion release surfaces. It would be desirable to provide a silicone release surface for the fastening and/or release tape elements of diaper tapes which provides the low friction necessary for assembly of the diaper tape without distortion due to tape stretching, and at the same time to provide sufficiently high adhesion to meet the various needs of disposable diaper release tape manufacture and use.

To provide such a surface for tapes, particularly polypropylene film tapes, is the purpose of the instant invention.

SUMMARY OF THE INVENTION

The present invention is directed to substrate films, including tapes which provide release surfaces exhibiting an excellent balance of friction and adhesion properties which enhance the production of diaper tapes. The contemplated products include silicone release coated polypropylene films for use as release tape and/or the fastening tape of a diaper tape assembly combination for use in the fabrication of disposable diapers.

The release compositions are based on a reactive silicone system comprising at least 15% by weight of a reactive polydialkyl siloxane, preferably a reactive polydimethyl siloxane, at least 40% by weight of a reactive silicone high adhesion agent (controlled release additive or CRA) and a crosslinking agent. The composition contains a suitable noble metal catalyst and reacts on application of heat to form a crosslinked surface having a coefficient of friction less than about 0.7 lb./2 inch and release greater than about 50 g/in.

The preferred release compositions comprise from about 25% to about 50% by weight reactive polydialkyl siloxane, preferably polydimethyl siloxane, and from about 75% to about 50% by weight of a reactive silicone high adhesion agent, and are preferably platinum catalyzed.

Although described herein in terms of tape, particularly diaper tape applications, the release surface of the invention may be provided on any support including both sides thereof including roll and sheet stock formed of paper and various polymeric materials.

THE DRAWING

The attached drawing illustrates the general assembling of a diaper tape showing the release and fastening surfaces.

DETAILED DESCRIPTION

The present invention is based on a reactive silicone system which provides, when cured (reacted) a release coating which aggressively bonds to a polypropylene surface and which offers a level of friction sufficiently low for passage over fixed processing surfaces, such as metal directing bars, and a sufficiently high adhesion level to prevent premature unwinding of a tape from its roll during manufacture of disposable diaper tapes and to prevent premature separation of the fastening tape from the release tape in a total diaper tape assembly.

With reference to the attached drawing, a diaper tape assembly 10 consists of a release tape 12 and a fastening tape 14. The release tape 12 consists of a release surface 16 and a pressure-sensitive adhesive layer 18 at opposite sides of a self supporting film or of a tape 20 normally a polyolefin, preferably polypropylene. The fastening tape 14 consists of a laminate of pressure-sensitive adhesive layer 22 and a release surface 24 on opposed sides of a film or tape 26 preferably also a polyolefin and preferably polypropylene. The release tape 12 is joined to a fastening tape at juncture 28 forming a "Y" configuration. The end of fastening tape 14 is longer, which is required to enable its end to be folded upon itself and form tab 30 used to separate the extended part of the fastening tape 32 from the release surface 16 of release tape 12. The facing adhesive surfaces 34 and 36 of release tape 12 and fastening tape 14 are secured in opposed exposed surfaces of a diaper shell (not shown). The extended segment 32 of the fastening tape folds over and is adhered to a release surface 16 of the release tape 12 until use.

While the present invention is directed to a release surface useful for both the release and fastening tapes, it is particularly directed to the release surface of release tapes as it is the release tape that must provide a low friction, high release surface to enable processability during manufacture, and a surface that will secure and hold the pressure-sensitive adhesive 22 of the fastening tape until use.

The major constituents of the release system are a reactive polydialkyl siloxane, a reactive silicone high adhesion agent, a crosslinking agent and a Group VIII metal catalyst.

The polydialkyl siloxanes are random alkenyl-reactive siloxanes, preferably reactive polydimethyl siloxanes, of the formula:

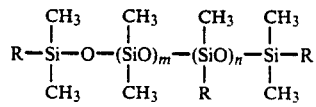

wherein each R is independently alkenyl of from 2 to about 6 carbon atoms and where m and n are independent integers. The polydialkyl siloxanes preferably have a viscometric average molecular weight in excess of about 300,000 centipoise (cps), preferably from about 300,000 to about 1,000,000 ops or more, and are present in an amount of at least 21% by weight, preferably from about 25% to about 50% by weight, of the release coating.

The reactive silicone high adhesive agent is based on a copolymer of monofunctional silicone units of the formula:

$$R'_3SiO_{\frac{1}{2}}$$

and tetrafunctional units of the formula:

$$SiO_{4/2}$$

where R' is an alkyl or alkenyl group containing from 1 to about 6 carbon atoms. The copolymer is dispersed in a reactive organic diluent and typically uncondensed providing, thereby, alkenyl unsaturation. The reactive organic diluent is typically an unsaturated compound such as dimethyl maleate, decylvinylether, dodecylvinylether, camphene, m-bisisopropenyl-benzene, and the like, preferably alpha-olefins containing from about 12 to about 18 carbon atoms. A minor amount may be polydimethyl siloxane and/or alkenyl - reactive siloxane as described above. The contemplated reactive silicone control release agents are described in detail in European Patent Application 108,208 of May 16, 1984, incorporated herein by reference.

The reactive silicone high adhesion agent is present in an amount of at least about 40% by weight of the total silicone release system, preferably from about 50% to about 75% by weight.

A third component of the silicone system, which may be part of the reactive polydialkyl siloxane and/or silicone high adhesion agent or separately added, is a random silicone hydride cross-linking agent of the general formula:

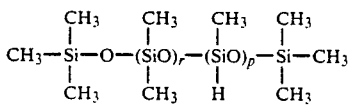

where r and p are independent integers in which r may be zero and p is 3 or more. Concentration may be varied widely but is typically less than about 10% by weight of the total silicone constituents. The presence of the crosslinking agent is necessary and in a sufficient quantity to obtain an effectively cured release coating which is preferably formed in line with adhesive application.

The silicone systems are applied from a solvent base and react by thermally induced addition-cure (hydrosilation) to furnish a cured silicone release surface.

The whole hydrosilation or cure reaction is catalyzed by silicone soluble complexed compounds of Group VIII transition metals, particularly platinum. In normal use, a small amount of inhibitor is added to prevent premature reaction of the mixed silicone system. This inhibitor is removed or made ineffectual during the thermal curing process. The catalyst may be provided in admixture with silicone components or be as a separate additive, typically in a solvent.

Components of the silicone release composition are combined in proportion to obtain a product having a coefficient of friction of less than about 0.7 lb./2 inches as determined by drawing a sled measuring 2×6 inches made of stainless steel loaded with an additional weight of 500 grams over a release surface measuring 2×14 inches. To provide a sufficiently high adhesion level for diaper processing purposes and consumer use, the composition requires a 180° peel of at least 50 grams per inch at a peel rate of 12 inches per minute (Pressure Sensitive Tape Council Test No. 4). Weight ratio (dry) of the reactive polydialkyl siloxane to reactive siloxane high adhesion agent in the curable composition will normally range from about 1:1 to about 1:5. In the absence of the reactive diluent provided with the silicone high adhesion agent, there is not provided the proper balance of adhesion of the release to polyolefin (polypropylene) film, low friction, and high adhesion levels. For this purpose, the following Examples and Controls illustrate the invention wherein the variable components of the composition are the silicone systems used and relative concentrations. In each instance, the formulated silicone release compositions, were coated from a heptane solution onto the glossy surface of a polypropylene film, cured at a temperature of from 175° F. to about 200° F., and evaluated as set forth below.

EXAMPLES 1 TO 8 AND CONTROLS 1 TO 8

The following Examples (Examples 1 to 8) are illustrative of the invention in exhibiting properties of low friction and high adhesion. As Controls, there are provided Controls 1 to 4 which are representative of conventional solvent based silicone release compositions which exhibited an acceptable coefficient of friction (COF) but too low of an adhesion level, and Controls 5 to 8 which are representative of conventional, 100 per cent solids silicone release compositions which exhibited an unacceptably high coefficient of friction. In the following table:

Pt-Cat = GE 8010, platinum catalyst concentrate in solvent;

Si-1 = GE 5030, a silicone control release copolymer in a reactive diluent;

Si-2 GE 4300C, a polyhydromethylsiloxane crosslinker;

Si-3 GE 4330, a vinyl terminated reactive high molecular weight polydimethylsiloxane viscometric molecular weight greater than 300,000 CPS;

Si-4 GE 4335, a silicone control release dissolved in a non-reactive solvent;

Si-5 GE 5010 relatively low viscometric molecular weight (less than about 15,000 CPS) vinyl pendant and terminated polydimethyl siloxane;

RT = Room Temperature;

Test Tape A = A diaper fastening tape having a tackified elastomer pressure-sensitive adhesive Test Tape B = Another diaper tape having a tackified elastomer pressure-sensitive adhesive In each instance, the silicone release was applied to the glossy side of a polypropylene substrate and cured at 180° F. for 45 seconds.

As will be appreciated reactive silicones and catalyst compositions of other manufacturers which perform on an equivalent basis may be substituted for any specifically described above.

TABLE 1

| | Examples 1-8 | | | | | | | |
|---|---|---|---|---|---|---|---|---|
| | Ex. 1 | Ex. 2 | Ex. 3 | Ex. 4 | Ex. 5 | Ex. 6 | Ex. 7 | Ex. 8 |
| FORMULA | | | | | | | | |
| Pt-Cat | 0.10 | 0.20 | 0.30 | 0.40 | 0.10 | 0.20 | 0.30 | 0.40 |
| Si-1 | 1.50 | 3.00 | 4.50 | 6.00 | 1.50 | 3.00 | 4.50 | 6.00 |
| Si-2 | 0.28 | 0.51 | 0.74 | 0.90 | 0.28 | 0.51 | 0.74 | 0.98 |
| Si-3 | 1.50 | 1.50 | 1.50 | 1.50 | 1.50 | 1.50 | 1.50 | 1.50 |
| Si-4 | | | | | | | | |
| Si-5 | | | | | | | | |
| Heptane | 93.50 | 92.00 | 90.50 | 89.00 | 93.50 | 92.00 | 90.50 | 89.00 |
| Si-1/Si-3 Ratio | 1.00 | 2.00 | 3.00 | 4.00 | 1.00 | 2.00 | 3.00 | 4.00 |
| SMEAR/RUB OFF | no/no | no/no | no/no | no/no | no/no | no/no | no/no | no/no |
| COF (Lb/2 Inch Width) | | | | | | | | |
| 500 g | 0.45 | 0.45 | 0.48 | 0.50 | 0.43 | 0.53 | 0.50 | 0.50 |
| 1000 g | 0.65 | 0.70 | 0.75 | 0.80 | 0.68 | 0.85 | 0.80 | 0.83 |
| TEST TAPE - A | | | | | | | | |
| RT Release | 103 | 376 | 617 | 706 | 57 | 304 | 586 | 728 |
| RT Peel | 5.0 | 5.2 | 5.1 | 5.0 | 4.2 | 4.5 | 4.4 | 4.4 |
| KEIL Release | 83 | 523 | 1115 | 1291 | 56 | 430 | 1010 | 1304 |
| KEIL Peel | 5.8 | 6.5 | 6.0 | 6.5 | 4.6 | 5.1 | 6.2 | 5.8 |
| TEST TAPE - B | | | | | | | | |
| RT Release | 34 | 118 | 559 | 826 | 34 | 113 | 614 | 997 |
| RT Peel | 5.1 | 5.9 | 5.2 | 4.7 | 5.2 | 4.3 | 4.5 | 4.4 |
| KEIL Release | 45 | 220 | 1008 | 1145 | 76 | 744 | 1223 | 1359 |
| KEIL Peel | 3.9 | 2.9 | 4.1 | 4.0 | 3.5 | 4.0 | 4.0 | 4.0 |
| Aging, Hrs. | 0 | 0 | 0 | 0 | 6 | 6 | 6 | 6 |

| | Controls 1-8 | | | | | | | |
|---|---|---|---|---|---|---|---|---|
| | 1 | 2 | 3 | 4 | 5 | 6 | 7 | 8 |
| FORMULA | | | | | | | | |
| Pt-Cat | | | | | 0.34 | 0.34 | 0.34 | 0.34 |
| Si-1 | | | | | 5.25 | 5.25 | 5.25 | 5.25 |
| Si-2 | 0.10 | 0.10 | 0.10 | 0.10 | 1.27 | 0.96 | 0.72 | 0.60 |
| Si-3 | 5.00 | 5.00 | 5.00 | 5.00 | | | | |
| Si-4 | 0.13 | 0.25 | 0.50 | 1.00 | | | | |
| Si-5 | | | | | 4.75 | 4.75 | 4.75 | 4.75 |

TABLE 1-continued

| | | | | | | | | |
|---|---|---|---|---|---|---|---|---|
| Heptane | 95.00 | 93.50 | 70.00 | 70.00 | 70.00 | 70.00 | | 70.00 |
| Si-1/Si-3 Ratio | | | | | | | | |
| SMEAR/RUB OFF | no/no | no/no | no/no | no/no | no/no | no/no | no/no | no/no |
| COF (Lb/2 Inch Width) | | | | | | | | |
| 500 g | 0.40 | 0.40 | 0.48 | 0.45 | 2.30 | 1.40 | 1.40 | 1.30 |
| 1000 g | 0.60 | 0.60 | 0.70 | 0.65 | 3.50 | 3.00 | 2.40 | 2.30 |
| TEST TAPE - A | | | | | | | | |
| RT Release | 12 | 8 | 21 | 83 | | | | |
| RT Peel | 4.1 | 4.2 | 4.2 | 3.8 | | | | |
| KEIL Release | 22 | 12 | 27 | 66 | | | | |
| KEIL Peel | 6.4 | 6.0 | 5.7 | 5.0 | | | | |
| TEST TAPE - B | | | | | | | | |
| RT Release | | | | | | | | |
| RT Peel | | | | | | | | |
| KEIL Release | | | | | | | | |
| KEIL Peel | | | | | | | | |
| Aging, Hrs. | 0 | 0 | 0 | 0 | 0 | 0 | 0 | 0 |

I claim:

1. A release surface comprising a substrate supporting a cured release coating formed from a reactive silicone system comprising at least 15% by weight of the silicone system f a reactive polydialkyl siloxane, at least 40% by weight of the silicone system of a reactive silicone high adhesive agent, said silicone high adhesion agent comprising a copolymer of monofunctional silicone units of the formula:

$$R'_3SiO_{1/2}$$

and tetrafunctional units of the formula:

$$SiO_{4/2}$$

where $R^{40}$ is an alkyl or alkenyl group containing from 1 to about 6 carbon atoms dispersed in a reactive organic diluent and a silicone hydride crosslinking agent, cure occurring by hydrosilation reaction of the reactive silicone system, reactive diluent and silicone hydride crosslinking agent in the presence of Group VIII metal catalyst, said polydialkyl siloxane and silicone high adhesion agent being present in proportion to provide a cured release coating having a coefficient of friction of less than about 0.7 lb/2 inch and a release greater than about 50 g/in.

2. A release surface as claimed in claim 1 in which the reactive polydialkyl siloxane is present in an amount of from about 25 to about 50% by weight of the reactive silicone system.

3. A release surface as claimed in claim 1 in which the reactive polydialkyl siloxane is a polydimethyl siloxane.

4. A release surface as claimed in claim 1 in which the reactive polydialkyl siloxane has a viscometric average molecular weight in excess of 300,000 cps.

5. A release surface as claimed in claim 3 in which the reactive polydimethyl siloxane has a viscometric average molecular weight of from about 300,000 to about 1,000,000 cps.

6. A release surface as claimed in claim 1 in which the reactive silicone high adhesion agent is present in an amount of from about 50 to about 75% by weight of the reactive silicone system.

7. A release surface as claimed in claim 2 in which the reactive silicone high adhesion agent is present in an amount of from about 50 to about 75% by weight of the reactive silicone system.

8. A release surface as claimed in claim 3 in which the reactive silicone high adhesion agent is present in an amount of from about 50 to about 75% by weight of the reactive silicone system.

9. A release surface as claimed in claim 5 in which the reactive silicone high adhesion agent is present in an amount of from about 50 to about 75% by weight of the reactive silicone system.

10. A release surface comprising a substrate supporting a cured release coating formed from a reactive silicone system comprising from about 25 to about 50% by weight of the silicone system of an alkenyl reactive siloxane of the formula:

$$R-\underset{\underset{CH_3}{|}}{\overset{\overset{CH_3}{|}}{Si}}-O-(\underset{\underset{CH_3}{|}}{\overset{\overset{CH_3}{|}}{SiO}})_m-(\underset{\underset{R}{|}}{\overset{\overset{CH_3}{|}}{SiO}})_n-\underset{\underset{CH_3}{|}}{\overset{\overset{CH_3}{|}}{Si}}-R$$

wherein each R is independently an alkenyl containing from 2 to about 6 carbon atoms and m and n are independent integers; from about 75 to about 50% by weight of the silicone system of a reactive silicone high adhesion agent, said silicone high adhesion agent comprising a copolymer of monofunctional silicone units of the formula:

$$R'_3SiO_{\frac{1}{2}}$$

and tetrafunctional units of the formula:

$$SiO_{4/2}$$

where R' is an alkyl or alkenyl group containing from 1 to about 6 carbon atoms dispersed in a reactive organic diluent and a silicone hydride crosslinking agent, cure occurring by hydrosilation reaction of the reactive silicone system, reactive diluent and silicone hydride crosslinking agent in the presence of Group VIII metal catalyst, said polydialkyl siloxane and silicone high adhesion agent being present in proportion to provide a cured release coating having a coefficient of friction of less than about 0.7 lb/2 inch and a release greater than about 50 g/in.

11. A release surface as claimed in claim 10 in which the reactive polydialkyl siloxane is a polydimethyl siloxane.

12. A release surface as claimed in claim 10 in which the reactive polydialkyl siloxane has a viscometric average molecular weight in excess of 300,000 cps.

13. A release surface as claimed in claim 11 in which the reactive polydimethyl siloxane has a viscometric average molecular weight of from about 300,000 to about 1,000,000 cps.

14. In the combination of a tape face material having on one surface thereof a pressure sensitive adhesive and on the opposed surface thereof a cured release coating, the improvement which comprises providing as the cured release coating formed from a reactive silicone system comprising at least 15% by weight of the silicone system of a reactive polydialkyl siloxane, at least 40% by wight of the silicone system of a reactive silicone high adhesion agent, said silicone high adhesion agent comprising a copolymer of monofunctional silicone units of the formula:

$$R'_3RiO_{\frac{1}{2}}$$

and tetrafunctional units of the formula:

$$SiO_{4/2}$$

where R' is an alkyl or alkenyl group containing form 1 to about 6 carbon atoms dispersed in a reactive organic diluent and a silicone hydride crosslinking agent, cure occurring by hydrosilation reaction of the reactive silicone systems, reactive diluent and silicone hydride crosslinking agent in the presence of Group VIII metal catalyst, said polydialkyl siloxane and silicone high adhesion agent being present in proportion to provide a cured release coating having a coefficient of friction of less than about 0.7 lb/2 inch and a release greater than about 50 g/in.

15. A release surface as claimed in claim 14 in which the reactive polydialkyl siloxane is present in an amount of from about 25 to about 50% by weight of the reactive silicone system.

16. A release surface as claimed in claim 14 in which the reactive polydialkyl siloxane is a polydimethyl siloxane.

17. A release surface as claimed in claim 14 in which the reactive polydialkyl siloxane has a viscometric average molecular weight in excess of 300,000 cps.

18. A release surface as claimed in claim 14 in which the reactive polydimethyl siloxane has a viscometric average molecular weight of from about 300,000 to about 1,000,000 cps.

19. In a diaper tape construction consisting of the combination of a fastening tape and a release tape each comprising a polypropylene tape face material having on the opposed surface thereof a cured silicone release coating which comprises providing as the cured release coating a cured coating formed from a reactive silicone system comprising at least 15% by weight of the silicone system of a reactive polydialkyl siloxane, at least 40% by weight of the silicone system of a reactive silicone high adhesion agent, said silicone high adhesion agent comprising a copolymer of monofunctional silicone units of the formula:

$$R'_3SiO_{178}$$

and tetrafunctional units of the formula:

$$SiO_{4/2}$$

where R' is an alkyl or alkenyl group containing from 1 to about 6 carbon atoms dispersed in a reactive organic diluent and a silicone hydride crosslinking agent, cure occurring by hydrosilation reaction of the reactive silicone system, reactive diluent and silicone hydride crosslinking agent in the presence of Group VIII metal catalyst, said polydialkyl siloxane and silicone high adhesion agent being present in proportion to provide a cured release coating having a coefficient of friction of less than about 0.7 lb/2 inch and a release greater that about 50 g/in.

* * * * *

UNITED STATES PATENT AND TRADEMARK OFFICE
CERTIFICATE OF CORRECTION

PATENT NO. : 5,080,973

DATED : January 14, 1992

INVENTOR(S) : Thanh V. Nguyen

Page 1 of 2

It is certified that error appears in the above-identified patent and that said Letters Patent is hereby corrected as shown below:

ABSTRACT, line 7, after "and" insert -- the --.

In the Specification

Column 1, line 49, change "involve" to -- involves --.

Column 2, lines 5,6, change "fastening tape/the release tape" to -- fastening tape/release tape --.

Column 2, line 36, after "coating" change "do" to -- does --.

Column 4, line 12, change "ops" to -- cps --.

Column 6, line 26, after "adhesive" insert a semicolon.

Column 6, line 28, after "adhesive" insert a period.

In the Claims

Column 7, line 22, after "system" change "f" to -- of --.

Column 7, line 29, change "$R'_3SiO_{178}$" to -- $R'_3SiO_{1/2}$ --.

Column 7, line 34, change "$R^{40}$" to -- $R'$ --.

Column 8, line 58, change "inch" to -- inches --.

Column 9, line 10, change "wight" to -- weight --.

UNITED STATES PATENT AND TRADEMARK OFFICE
CERTIFICATE OF CORRECTION

PATENT NO. : 5,080,973

DATED : January 14, 1992

INVENTOR(S) : Thanh V. Nguyen

It is certified that error appears in the above-identified patent and that said Letters Patent is hereby corrected as shown below:

Column 9, line 15, change "$R'_3RiO_{1/2}$" to -- $R'_3SiO_{1/2}$ --.

Column 9, line 20, after "containing" change "form" to -- from --.

Column 9, line 39, change "inch" to -- inches --.

Column 10, line 21, change "$R'_3SiO_{178}$" to -- $R'_3SiO_{1/2}$ --.

Column 10, line 36, change "inch" to -- inches --.

Signed and Sealed this

Third Day of August, 1993

Attest:

MICHAEL K. KIRK

Attesting Officer

Acting Commissioner of Patents and Trademarks